United States Patent [19]

Engelson

[11] Patent Number: 4,884,579
[45] Date of Patent: Dec. 5, 1989

[54] CATHETER GUIDE WIRE

[75] Inventor: Erik T. Engelson, Palo Alto, Calif.

[73] Assignee: Target Therapeutics, San Jose, Calif.

[21] Appl. No.: 182,870

[22] Filed: Apr. 18, 1988

[51] Int. Cl.⁴ .............................................. A61B 5/02
[52] U.S. Cl. .................................. 128/772; 128/657; 604/170
[58] Field of Search ............... 128/344, 656, 657, 772; 604/170, 281, 282

[56] References Cited

U.S. PATENT DOCUMENTS

| 3,789,841 | 2/1974 | Antoskiw | 128/772 |
| 4,616,652 | 10/1986 | Simpson | 128/772 X |
| 4,619,274 | 10/1986 | Morrison | 128/772 |

FOREIGN PATENT DOCUMENTS 2401668 4/1979 France ................... 128/772

Primary Examiner—Dalton L. Truluck
Attorney, Agent, or Firm—Peter J. Dehlinger

[57] ABSTRACT

A catheter guide wire designed for use in guiding a catheter to a target site along a tortuous vessel path. The guide wire has a relatively long, torqueable proximal wire section, a more flexible intermediate section, and a most flexible distal end section designed to be advanced across sharp-bend vessel junctions. The intermediate section has greater lubricity than the adjacent proximal and distal sections. The greater frictional coefficient in the distal end segment acts to anchor the end of the wire in a branch vessel, when the guide wire has been advanced across the sharp-bend vessel junction, and the catheter is threaded axially over the wire, while the more lubricious surface of the intermediate section gives reduced sliding friction within the catheter during such advance. The invention also includes a catheter device containing the guide wire and catheter.

15 Claims, 2 Drawing Sheets

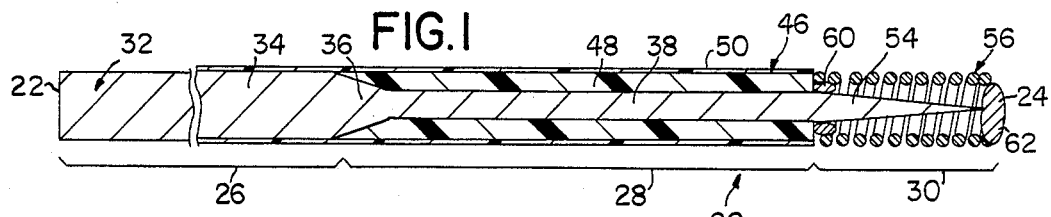
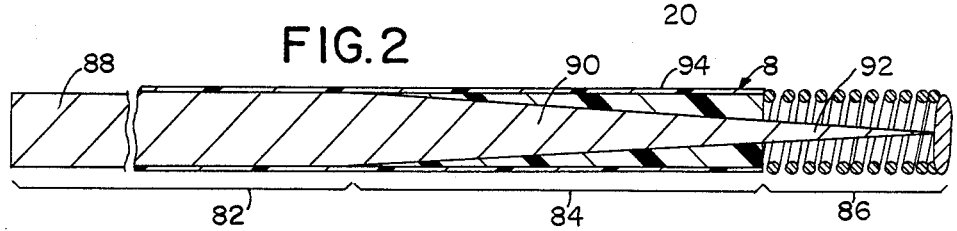
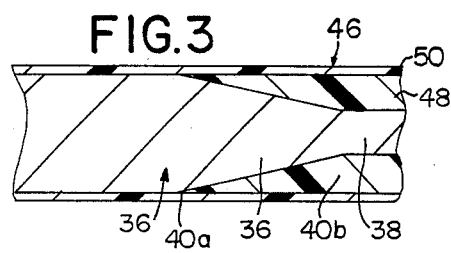
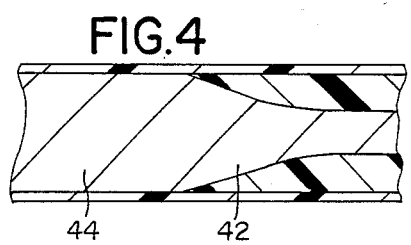
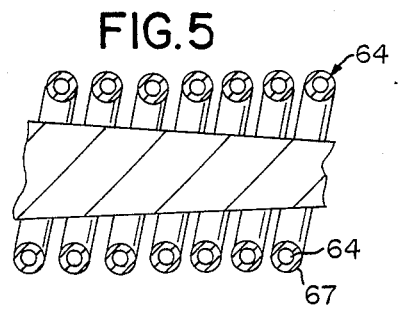
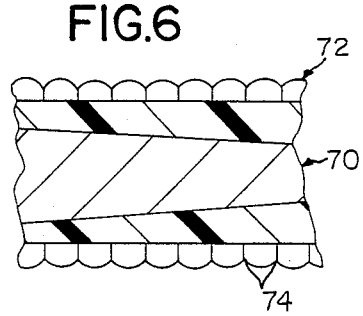
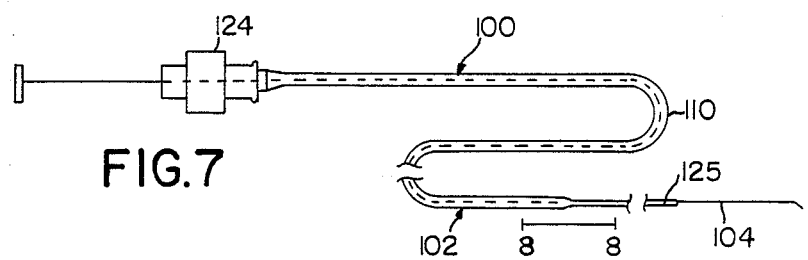

CATHETER GUIDE WIRE

1. FIELD OF THE INVENTION

The present invention relates to a catheter guide wire for accessing a tissue target site via a small-lumen tortuous path within a target tissue.

2. BACKGROUND OF THE INVENTION

Catheters are being used increasingly as a means for delivering diagnostic or therapeutic agents to internal target sites that can be accessed through the circulatory system. For example, in angiography, catheters are designed to deliver a radio-opaque agent to a target site within a blood vessel, to allow radiographic viewing of the vessel and blood flow characteristics near the release site. For the treatment of localized disease, such as solid tumors, catheters allow a therapeutic agent to be delivered to the target site at a relatively high concentration, with minimum overall side effects. Methods for producing localized vaso-occlusion in target tissue regions, by catheter injection of a vaso-occlusive agent, have also been described (co-owned U.S. patent application for "Hyperthermic Treatment of Tumors", Ser. No. 751,605, filed 2 July 1985).

Often the target site which one wishes to access by catheter is buried within a soft tissue, such as brain or liver, and can be reached only by a tortuous route through small vessels or ducts—typically less than about 3 mm lumen diameter—in the tissue. The difficulty in accessing such regions is that the catheter must be quite flexible, in order to follow the tortuous path into the tissue, and at the same time, stiff enough to allow the distal end of the catheter to be manipulated from an external access site, which may be as much as a meter or more from the tissue site.

Heretofore, two general methods for accessing such tortuous-path regions have been devised. The first method employs a highly flexible catheter having a dilated or dilatable distal end. A major limitation of this method is that the catheter will travel in the path of highest blood flow rate, so many target sites with low blood flow rates cannot be accessed.

In the second prior art method, a torqueable guide wire having a distal bend is guided, by alternately rotating and advancing the wire, to the target site. With the wire in place, a thin-walled catheter is then advanced along the wire until the distal catheter end is positioned at the target site. Once the catheter is advanced, the guide wire may be withdrawn to allow fluid delivery or withdrawal through the catheter. An important advantage of this method is the ability to control the location of the catheter along a vascular pathway.

Several types of guide wires for use in catheter placement have been proposed. The simplest type of wire is a preferred diameter of between about 8–40 mils (thousandths of an inch). The distal end of the wire may be provided with a bent tip which can be oriented, by means of guide structure at the proximal end, to guide the wire along a selected vascular path. Ideally, torque transmission should be controlled, such that a selected wire rotation at the wire's proximal end produces a corresponding rotation of the distal end. Because of their greater flexibility, smaller diameter wires, e.g., having diameters of between about 8–18 mils, may be required for accessing small-vessel and/or tortuous-path regions. However, if the wire is too thin along its entire length, it may be difficult to transmit torque in a controlled manner along the entire wire length. Further, the wire may buckle with axial movement due to low column strength.

Constant-diameter guide wires having a wire core encased in a flexible polymer tubing have also been proposed. The flexible tubing acts to increase the column strength of the wire core without significantly reducing overall flexibility. As a result, the problem of wire buckling, especially in small-diameter wires, is lessened. Biocompatible polymers, such as TEFLON®, polyolefins, and polyurethane have been suitable.

More recently, guide wires which have multiple variable-thickness steps along the wire length have been proposed. Wires of this type have the advantage that the proximal end region, where greater torsional strength is required, have relatively large diameters—e.g., between about 20–40 mils, and the distal end region, where greater flexibility is required, have progressively smaller diameters. Typically, a wire of this type will have different diameter segments extending collectively over an approximately 25–60 cm distal portion of the wire, and a short (typically 1–3 cm) tapered transition zone across each step. The tapered zones are typically formed by centerless grinding in which the wire is placed between two counter-rotating grinding wheels whose confronting grinding surfaces are angled slightly to produce the desired taper over the width of the wheels.

If the tapered transition is relatively steep and/or transition occurs in a region where a sharp vessel bend is encountered, the wire may bend sharply in the step (transition) zone, due to the differential bending modulus at the transition zone. If the catheter on the wire has already been advanced past the point of the bend, the catheter may deform at the wire bend, making further catheter advance along the wire difficult or impossible. Further, torqueability in the wire is reduced at the region of a sharp bend, since torque tends to be transmitted through the angle of the bend, rather than along the axis of the wire.

Guide wires having extended sections of continuous taper have also been disclosed. The long tapered regions have less tendency to undergo irreversible bending than relatively short tapered wire sections. However, problems of wire buckling and difficulty in sliding the wire within the catheter in a tortuous path limit the ability of the wire and catheter to reach deep tissue sites.

The problems of advancing a catheter along a guide wire in a small-lumen tortuous tissue pathway are also due to limitations in prior art catheter construction. If the catheter is relatively rigid, it cannot track over the final distal portion of the wire in the tortuous path region, because catheter advancement buckles the wire in a narrow turn, or because catheter advancement pulls the wire out of the distal vessels. On the other hand, catheters having more flexible shafts, such as those used in balloon flow-directed devices, lack the column-strength in the catheter's proximal section to be advanced over the guide wire without buckling.

3. SUMMARY OF THE INVENTION

It is therefore one general object of the invention to provide a guide wire designed to overcome the above-discussed limitations in accessing the tortuous path tissue sites.

A more specific object of the invention is to provide such a guide wire for accessing soft tissue target sites, such as deep brain sites, which have heretofore been inaccessible to catheters.

Still another object of the invention is to provide a catheter device for delivery of an injectable fluid or particle suspension at a tissue site which can be accessed only by a tortuous vessel path, which may be defined by arteries, veins, or tissue ducts.

The invention includes, in one aspect, a guide wire designed for use in guiding a catheter to a target site along a tortuous vessel path which is at least about 20 cm long and which has sharp-bend vessel junctions. Such a path requires advancing a distal portion of the wire across the junction, then sliding the catheter over the advanced portion of the wire. The wire has three sections with progressively greater flexibility, and different lubricity or sliding properties. A flexible, torqueable proximal wire section is between about 50-250 cm in length and is formed of a proximal wire core segment having an outer diameter of between about 10-40 mils. A more flexible intermediate section has a length between about 20-60 cm and is formed from an intermediate wire-core segment having a reduced diameter of between about 4-20 mils and between about 10%-50% of the core's proximal segment, and a flexible tube covering which encases the intermediate core segment. A most flexible distal end section has a length between about 1-10 cm and is formed from a distal wire core segment having a reduced diameter of between about 2-6 mils, and a flexible sleeve covering the distal end segment and providing column strength thereto. The intermediate section has a low-friction polymer surface provided by the covering which makes the section more lubricious than the adjacent distal end segment.

In a preferred embodiment, the proximal wire core segment is between about 10-20 mils, the intermediate wire core segment has an average diameter of between about 4-8 mils, and the distal wire core segment has a diameter of between about 2-5 mils. The intermediate wire core segment has a substantially constant diameter along its length, and includes a relatively short region of taper between the constant-diameter portions of the distal and intermediate wire core segment. The distal wire core segment has a substantially continuous taper along its length. The guide wire may have a substantially constant outer diameter along its length, or a slight reduction in diameter progressing toward the distal end.

Also in a preferred embodiment, the flexible polymer covering in the intermediate section is a polymer tube which is effective to increase the column strength of the intermediate section, and which has a low-friction polymer coating. The sleeve covering is a helical coil formed from a radio-opaque metal strand material.

In another aspect, the invention includes a catheter device for use in accessing a target site along a tortuous vessel path. The device includes a guide wire of the type described above and a catheter designed to be advanced over the wire, with such advanced to the target site.

In a preferred embodiment, the catheter has a relatively stiff proximal tube segment dimensioned to track the wire along its proximal end section, and a relatively flexible distal tube segment constructed and dimensioned to track the wire along its intermediate and distal end sections. Also in a preferred embodiment, the catheter and wire have a substantially constant radial clearance of about 2-5 mils.

These and other objects and features of the invention will become more fully appreciated when the following detailed description of the invention is read in conjunction with the accompanying drawings.

BRIEF DESCRIPTION OF THE DRAWINGS

FIG. 1 shows fragmentary portions of a guide wire constructed according to one embodiment of the present invention;

FIG. 2 shows fragmentary portions of a guide wire constructed according to another embodiment of the invention;

FIGS. 3 and 4 are enlarged side views of a discrete (FIG. 3) and continuous (FIG. 4) taper in the tapered region of an embodiment of the guide wire such as shown in FIG. 1;

FIGS. 5 and 6 are enlarged sectional views of different embodiments of flexible sleeves suitable for covering the distal end regions of the guide wires constructed according to the invention;

FIG. 7 shows a catheter device constructed according to the present invention;

DETAILED DESCRIPTION OF THE INVENTION

I. Guide Wire

Figure 8:
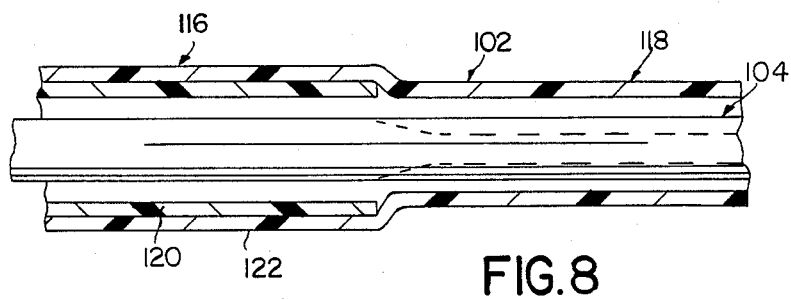
FIG. 8 shows an enlarged section of the catheter device in FIG. 7, taken along the region indicated at 8—8.

FIG. 1 shows a guide wire 20 constructed according to one embodiment of the invention. The wire is a flexible torqueable wire having an overall length of between about 70-300 cm between its proximal and distal ends 22, 24, respectively, and a maximum outer diameter of between about 8-40 mils (thousandths of an inch). The major portion of the wire is a flexible proximal section 26 whose overall length ranges from about 40-250 cm. This section is followed by a more flexible intermediate section 28 having a length between about 15-60 mils, and a most flexible distal end section 30 wose length is between about 1-10 cm. It will be appreciated that the wire is shown in greatly exaggerated radial scale, and that a major portion of the distal end section has been cut away.

A wire core 32 in the guide wire is formed of a flexible, torqueable wire filament material, such as stainless steel. The diameter of the wire core, at its maximum, is between about 8-40 mils. The segment of the core forming the proximal section of the guide wire, indicated at 34, has a substantially uniform diameter along its length, and corresponds to the maximum diameter of the core, i.e., between 8-40 mils.

Within the intermediate section of the wire, the core is tapered from the proximal-section diameter down to a reduced diameter which is preferably about 4-20 mils and between about 10%-50% of the core's proximal segment diameter. Thus, for example, where the proximal section core diameter is 18 mils, the core tapers to a minimum of between about 2-9 mils.

In the embodiment shown in FIG. 1, the taper in the core occurs over a relatively short tapered segment 36 which is followed by a reduced-diameter segment 38 having a substantially constant diameter along its length. The length of the tapered segment is typically between about 10%–50% that of the constant-diameter, and the two segments together make up the length of the intermediate wire section, i.e., about 20–60 cm.

The tapered segment in the FIG. 1 wire embodiment is shown in enlarged view in FIG. 3. This type of taper may be thought of as a discrete taper, in that the profile of the tapered section wall is linear, and the segment intersects the opposed constant-diameter segments at discrete angles at the annular regions 40a, 40b in the figure. FIG. 4 shows a tapered segment 42 of a wire core 44 formed in accordance with another embodiment of the invention. Here the slope of the taper is continuously varying, and the segment has the generally S-shaped wall profile seen. The taper segment illustrated in FIG. 4 is generally preferred since it minimizes bending and torque-transmission differentials at ends of the tapered segment. Methods of forming the two types of tapers will be discussed below.

The two segments making up the core of the intermediate section of the wire are covered along their length by a flexible polymer covering 46. The major function of the covering is to provide a lubricious (low-friction) surface along the intermediate section, and more particularly, a surface which is more lubricious than the surface of the adjacent distal segment of the wire and of the wire core. The covering preferably also functions to provide column support to the reduced-diameter core in the intermediate section, to reduce the tendency of this section to buckle under axial compression.

Covering 46 is preferably formed of a polymer, such as TEFLON TM, polyolefin, or polyurethane which can be bonded or otherwise tightly affixed to the core wire, and which itself has a low-friction surface, as is the case for TEFLON TM, or whose surface can be coated with a low-friction surface. Other suitable coverings include a tube formed from virtually any polymer having exposed hydrogens, such as polyester, polyolefins, polycarbonate, polyvinylchloride, latex or silicon rubber, polystyrene, and polyacrylics, and a surface coating formed of a highly hydrophilic, low-friction polymer, such as polyvinylpyrrolidone (PVP), polyethyleneoxide, or polyhydroxyethylmethacrylate (polyHEMA) or copolymers thereof.

In the embodiment shown in FIG. 1, covering 46 is formed of a relatively thick-walled tubing 48 and a surface coating 50 of a low-friction polymer. The inner diameter of the tubing is such as to form a tight fit of the tubing on the wire core, and the outer diameter is substantially the same as that of the core wire proximal section. Thus the proximal and intermediate wire sections have substantially the same outer diameters, e.g., between about 8–40 mils. The segment of the tubing encasing tapered section 36 preferably has a complementary taper, as seen best in FIG. 3.

The low-friction polymer coating may also cover an adjacent portion of the wire's proximal section, as shown in FIG. 1. Typically, the coating will be applied to the 20–50 cm of the distal section core adjacent the intermediate section. Alternatively, the proximal section core may be coated with a less lubricious protective coating material, such as silicone coating or the like.

With continued reference to FIG. 1, distal section 30 of the wire has a length between about 1–10 cm and preferably has still greater flexibility than the intermediate wire section. The wire core in the distal section, referred to a segment 54, has a diameter which is substantially no greater than that of the intermediate section core, and preferably is tapered to a reduced diameter of between about 2–6 mils. In the embodiment shown in FIG. 1, the core has a linear taper over its entire length. Alternatively, the core may contain one or more discrete tapers.

The distal section portion of the core is fully or partially encased in a flexible sleeve. The sleeve shown in FIG. 1 is a soft, flexible helical coil 56 which is formed conventionally, e.g., as a winding of radio-opaque wire strand, such as platinum, gold, or tungsten strand. As shown, the coil extends from covering 46 to the distal end of the wire core. The coil preferably has a fixed-dimension inner diameter, as shown, or may be tapered, e.g., to match the taper in the core. Attachment of the coil to the core is preferably by two or three solder or weld joints, including a proximal joint 60 and a rounded distal joint 62. An intermediate joint (not shown) serves to transmit torque in the wire to the coil, to cause the end region of the guide wire to bend slightly at this solder joint, to allow the wire to be guided in a selected direction in a vessel network, by torqueing the proximal end of the wire. The core and coil can be irreversibly shaped, prior to use, to include wire bend useful in guiding the wire.

In addition to providing a mechanism for wire bending near the wire tip, the coil also gives the distal section of the wire increased column strength (in the axial direction), and reduces the chance of buckling in this section with axial compression. At the same time, the combined flexibility of the reduced diameter core and the coil are compatible with a series of sharp bends, as the wire is moved through a tortuous pathway in the target tissue. The rounded joint at the end of the wire acts to shield vessel walls from the sharp end of the wire core.

According to an important feature of the invention, the distal section of the wire, including the sleeve encasing the wire core in this section, is less lubricious, i.e., has a higher frictional coefficient, than that of the adjacent intermediate section. The higher-friction surface in this section functions specifically, during a catheter placement operation, to help anchor the distal section against a vessel wall at a vessel junction, as will be seen below. The higher friction can be achieved in a number of ways. Where the sleeve is a coil, the coiled surface inherently has a higher surface coefficient than a low-friction polymer coating.

FIG. 5 is an enlarged sectional view of a distal section of a wire such as shown in FIG. 1. The coil in the section, here indicated at 64, is formed as a helical winding of a radio-opaque strand 66 which has been precoated by a polymer cover 67. The polymer can be selected for low- or high-friction surface properties, to selectively vary the frictional properties of the sleeve. Alternatively, a coil formed from a bare strand may be coated, after attachment to the wire core, with a suitable protective polymer, such as silicon or the like.

In another embodiment, the sleeve in the distal segment may be a polymer tubing which is both flexible and capable of providing column strength to the distal-section wire core. The tubing, if formed to have a smooth wall, can be made from a variety of polymers, such as polyethylene, latex or the like, which have relatively high frictional coefficients. Alternatively, the sleeve may be formed with surface features which increase the frictional coefficient substantially. One such sleeve is shown in enlarged view in FIG. 6, showing a portion of a distal section similar to FIG. 5. Here the distal segment of the wire core, indicated at 70, is encased in a polymer tube 72 having a series of annular grooves, such as grooves 74 formed in its surface. It can be appreciated that these grooves provide increased tube flexibility as well as greater frictional coefficient. At the same time, the added column strength contributed by the tube is substantially preserved since axial compression on the tube acts to press the grooved regions against one another. The polymer sleeve is preferably provided with a radio-opaque band (not shown).

FIG. 2 shows a guide wire 80 constructed according to a second general embodiment of the invention. The wire has proximal, intermediate, and distal sections 82, 84, 86, respectively, and a wire core with corresponding core segments 88, 90, 92, respectively. The wire differs from that shown in FIG. 1 in that the wire core has a continuous, linear (or, alternatively, a continuous S-shaped curve) through the intermediate and distal sections rather than a shorter tapered segment and a longer reduced-diameter segment. The other features of the wire, including a polymer surface coating 94 which provides a low-friction surface over the intermediate section and an adjacent portion of the distal section, are substantially identical to those described above with reference to FIG. 1.

In forming the guide wire of the invention, the wire core is typically constructed by grinding a conventional, constant-diameter guide wire, such as is commercially available stainless steel wires. Step grinding can be used to form relatively short tapered segments, such as in forming the core used in the FIG. 1 wire. Methods of forming relatively long, continuously tapered cores (FIG. 2) and non-linear tapered regions (FIG. 4) have been described in co-owned PCT patent application for "Catheter and Tissue Accessing Method", W087/07493, filed Dec. 17, 1987, and incorporated herein by reference.

The flexible polymer tube covering the intermediate core is segment(s) can be applied to the core by conventional polymer spraying or dipping methods, or by attaching a preformed polymer tube to the core segment(s). The latter can be accomplished by attaching the tube to the core under heat shrinking conditions, or by securing the tube to the wire by a suitable wire/polymer bonding agent. As indicated above, the lubricious surface coating may be formed by the surface of the covering, or preferably, by applying a lubricious polymer surface coating. Such a surface coating, which preferably covers a portion of the distal section, can be applied by spraying or dipping, according to known methods.

II. Catheter Device

FIG. 7 shows a catheter device 100 constructed according to one aspect of the invention. The device includes a catheter 102 which will be described below, and a guide wire, here indicated at 104, of the type described above. The device is designed for accessing a target site which can be reached only along a small-lumen tortuous path within a target tissue, as will be described with reference to FIGS. 9-11 below.

With reference to FIG. 7, catheter 102 is formed of a flexible tube 110 which is dimensioned to receive the guide wire therethrough, as shown. In a preferred embodiment of the invention, the catheter has a relatively stiff proximal segment 116 which makes up between about 70%–95% of the total tube length, and a relatively flexible distal segment 118 which makes up the remaining approximately 5%–30% of the tube length. The construction of a catheter of this type has been detailed in above-mentioned PCT patent application for "Catheter and Tissue Accessing Method". Briefly, and with reference to FIG. 8, the relatively stiff section of the tube is composed of inner and outer coaxial tubes 120, 122 which are tight-fitting with respect to each other. The stiffness in the proximal segment is provided predominantly by tube 120. The inner, stiffer tube is preferably polypropylene or high-density polyethylene tubing having a final wall thickness (in the assembled catheter) of between about 2–4 mils. The outer, more flexible tube is preferably low-density polyethylene or silicone tubing, also having a preferred wall thickness of between about 2–4 mils.

With continued reference to FIG. 8, the inner diameter of the proximal segment is dimensioned, with respect to the guide wire, to provide sufficient wire clearance to allow the catheter to be moved easily over the wire in an axial direction, during catheter placement at the target site. The guide wire itself must have a relatively small diameter, to permit its guided movement along a tortuous path in a target tissue. In a preferred embodiment of the invention, the inner diameter of the catheter and the outer diameter of the guide wire are substantially constant along their lengths, and the clearance between the two is between about 2–5 mils. Thus, for example, a catheter designed for use with constant-diameter guide wire whose outer diameter is 18 mils has a preferred inner diameter of 20–25 mils, and more preferably 21–22 mils. The preferred clearance between the wire and inner wall of the segment reduces the tendency of the segment to buckle under compressional strain, since the wire provides column support against tube bending and crimping.

The optimal length of the proximal segment will vary according to the distance between the tissue region which is to be accessed by the catheter and the external body site at which the catheter is introduced. In a preferred embodiment, the total length of the catheter distal section is about the same length as that of the intermediate and distal wire sections combined.

Completing the description of the catheter, and with reference to FIG. 7, the free end of the proximal segment is attached to a fitting 124, such as a standard syringe fitting, for use in connecting a syringe to the catheter for fluid injection and withdrawal. At the distal end of the catheter, a radio-opaque band 125 (FIG. 9), such as a gold or platinum band, serves as a marker for following the position of the catheter radiographically.

III. Operation

The method of inserting the catheter into a tissue region which is reached by a tortuous path will be described now with reference to FIG. 9. The figure shows a region of soft tissue 140, such as brain tissue, containing a target site 142. Initially the guide wire, indicated at 104, is fed from a vascular access region adjacent the target tissue into a tissue-supply vessel 144 which extends into the tissue. In the present example, the tortuous path to the target site involves vessel 144, a vessel 146 which branches off vessel 144 at more than a right angle, and branch vessels 148 and 150 which each branch off the preceding vessel as shown. The path shown involves (a) a number of bends, some of which may be 90 degrees or more, (b) small vessels, typically with lumen diameters of less than about 3 mm, and (c) a total path length within the target tissue of at least about 10-20 cm.

In operation, the catheter device is threaded as a unit from an external access site through the vasculature to a region adjacent, but not into the tortuous path region of the target tissue. This is done, in the usual case where the catheter must pass through the cardiac aorta, by first placing a relatively large diameter guiding catheter (e.g., about 40 mils inner diameter) from the access site through the aorta and toward the target site. The present catheter device is then threaded through the guiding catheter past the aorta, where large vessel diameters and high blood flow volumes make it difficult to control the movement and position of the catheter. Once beyond the guiding catheter, the catheter device can be advanced as a unit toward the target site. In general, the path from the access site to the region adjacent the tissue is easily accessible, in that sharp bends, small-lumen vessels, and/or soft tissue structure are not encountered.

Typically, when the tortuous path tissue region is reached, and particularly where sharp bends in the path are encountered, the wire is advanced ahead of the catheter. This is done by advancing the wire axially within the catheter and at the same time torqueing the wire to orient the bent tip of the wire in the direction of desired wire movement. After the wire has been so advanced, the catheter is then advanced over the wire until the catheter end is close to the wire end. This procedure is repeated until the wire and catheter have been fully advanced through the small-diameter tissue vessel region to the target tissue site.

Figure 9:
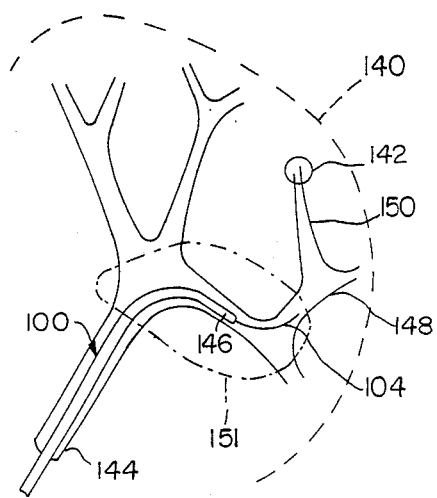
FIG. 9 illustrates a portion of a tortuous path in a soft tissue, and a catheter and guide wire being advanced along this path.
Figure 10:
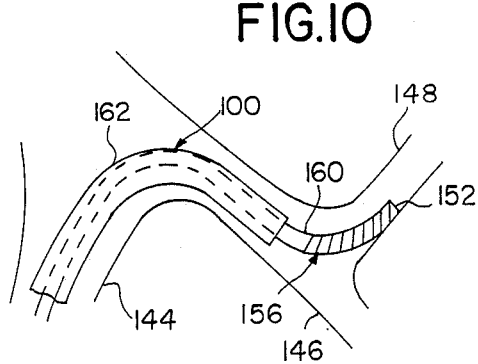
FIGS. 10 and 11 are enlarged regions of the FIG. 11 path, showing the steps in advancing the catheter through a sharp-bend junction in the path.
Figure 11:
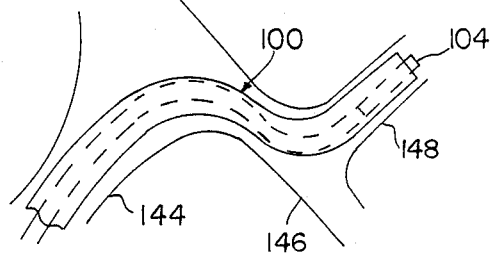

The features of the present invention which contribute to its ability to reach target sites along tortuous, soft-tissue paths can be appreciated from FIGS. 10 and 11, which show an enlarged portion of the region 140 indicated at dash-dot line 151 in FIG. 9. FIG. 10 shows the configuration of the catheter just after the distal section of the guide wire, indicated at 152, has been advanced ahead of the catheter into branch vessel 148 from vessel 146. The wire advance is achieved by first torquing the wire to orient the wire bend toward vessel 148, then moving the wire axially until the wire end moves into the branch vessel.

With the wire now held in its advanced position, the catheter is moved axially over the wire, in the direction of the vessel branch. It can be appreciated from FIG. 10 that movement of the catheter over the wire bend indicated at 156 causes this region of the wire to straighten, with the effect of increasing the force of the catheter distal section against the side of vessel 148. If the frictional force between the wire end region and the vessel is quite low, the end region of the wire within vessel 148 will now tend to slip out of the vessel, since the wire in this region is very flexible and easily capable of forming the type of rolling loop needed to excricate itself from vessel 148. For this reason, it is important that the surface of the distal region of the wire be a relatively high-friction surface.

It is also seen in FIG. 10 that the intermediate section of the wire, here indicated at 160, is contained largely within the catheter as the distal section of the wire is advanced through the vessel branch junction. At each bend in the catheter, the wire is pressed against the adjacent wall section of the catheter, as shown at bend 162. This pressure, it can be seen, increases the frictional resistance encountered in moving the wire axially within the catheter. In particular, it has been found with prior art wires that two or more such sharp bends in the catheter can make it impossible either to advance the guide wire relative to the catheter, during catheter placement, or to remove the wire after placement. According to an important feature of the invention, this problem is solved substantially by the low-friction surface on the intermediate wire section.

To illustrate, as the catheter in FIG. 10 is advanced over the distal section of the wire to the position shown in FIG. 11, only the most distal bend will involve a higher-friction portion of the wire, although the low-friction intermediate section may engage the catheter at several bands. Even along the distal wire section, the force needed to overcome the frictional resistance between the wire and distal catheter section is reduced by high flexibility of this segment. Similarly, the relatively high flexibility of the wire's intermediate section cooperates with the low-friction surface to facilitate axial movement of the wire in the catheter in a tortuous path.

Summarizing the important features of the invention, the greater flexibility in the distal and intermediate sections of the guide wire, related to the reduced-diameter feature of the wire core, allows the wire to be guided along a tortuous small-vessel path in a soft tissue, for accessing deep-tissue sites. The high flexibility in these sections also reduces frictional forces set up between the wire and catheter in bend regions along the access path.

The relatively high friction surface of the distal section is required in anchoring the distal section of the wire within a branch vessel, as the catheter is advanced across the junction. By contrast, the low-friction surface of the intermediate section acts to minimize the frictional resistance to axial wire movement through the catheter at regions of sharp bending in the catheter. This allows the wire to slide (and rotate) within the catheter with greater ease and reduces the liklihood that the wire will become immobilized within the catheter during a placement operation.

In a preferred embodiment of the invention, a portion of the proximal wire section adjacent the intermediate section is also provided with a low-friction surface, i.e., substantially lower than that of the wire core, to further reduce frictional resistance to wire movement. The more proximal portion of this section which will be handled by the user in guiding the wire from a body-access site to the target site preferably has a higher friction surface, to allow the wire to be manipulated without slippage.

Also in a preferred embodiment, the low-friction covering in the intermediate section is formed of a flexible tube which gives column support to the wire core. The greater column strength allows higher axial force to be applied to the wire in a catheter placement operation, without wire buckling. Where the guide wire and catheter each have constant diameters along their lengths, and a clearance of 2-5 mils between the two, the catheter also serves to resist wire buckling.

Additional advantages, in terms of target-site accessibility, are gained when the guide wire is used with the gradient-flexibility catheter described above. The greater flexibility in the distal region of the catheter allows the catheter to follow or track a wire bend with less axial force, since catheter deformation is reduced. Further, because the catheter end region flexes more easily, it exerts less force on the distal section of the wire when being advanced through a branch vessel junction, so the wire stays anchored in the branch vessel with less frictional resistance between the wire and vessel wall.

Preliminary clinical studies with the present invention indicate that the guide wire/catheter can be guided to deep brain sites which have been inaccessible previously. These sites typically involve catheter guidance along a 15-25 cm brain vessel pathway which has 2 to 6 vessel junctions where sharp turns are encountered, and spacing between adjacent turns of between about 1 to 5 cm.

While the invention has been described with respect to particular embodiments and uses, it will be appreciated that various changes and modifications can be made without departing from the scope of the invention.

It is claimed:

1. A catheter guide wire designed for use in guiding a catheter to a target site along a tortuous vessel path which is at least about 20 cm long and which has sharp-bend vessel junctions, requiring advancing a distal portion of the wire across the junction, then sliding the catheter over the advanced portion of the wire, said guide wire comprising
   a flexible, torqueable proximal wire section between about 50-250 cm in length and formed of a proximal wire core segment having an outer diameter of between about 10-40 mils,
   a more flexible intermediate section having a length between about 20-60 cm and formed from an intermediate wire-core segment having a reduced diameter of between about 4-20 mils and between about 10%-50% of the core's proximal segment, and a flexible polymer tube covering which encases the intermediate core segment and which provides column strength thereto, and
   a most flexible distal end section have a length between about 1-10 cm and formed from a distal wire core segment having a reduced diameter of between about 2-6 mils, and a flexible sleeve covering the distal end segment and providing column strength thereto,
   said intermediate section having a polymer surface which makes the section more lubriciuos than the adjacent distal end segment and said wire core.

2. The guide wire of claim 1, wherein the proximal wire core segment is between about 10-20 mils, the intermediate wire core segment has an average diameter of between about 4-8 mils, and the distal wire core segment has a diameter of between about 2-5 mils.

3. The guide wire of claim 2, wherein the intermediate wire core segment has a substantially constant diameter along a major portion of its length, and includes a relatively short region of taper between the constant-diameter portions of the distal and intermediate wire core segment.

4. The guide wire of claim 2, wherein the distal wire core segment has a substantially continuous taper along its length.

5. The guide wire of claim 1, which has a substantially constant outer diameter along its length.

6. The guide wire of claim 1, wherein said covering is composed of an inner polymer tube formed from one polymer material, and a surface coating formed from a second, more lubricious polymer material.

7. The guide wire of claim 6, wherein the intermediate section has an outer diameter which is substantially the same as that of the distal wire core segment.

8. The guide wire of claim 1, wherein said sleeve is a helical coil formed from a radio-opaques metal selected from the group consisting of platinum and gold.

9. The guide wire of claim 8, wherein the distal end section has an outer diameter which is substantially the same as that of the intermediate section.

10. A catheter guide wire designed for use in guiding a catheter to a target site along a tortuous vessel path which is at least about 20 cm long and which has sharp-bend vessel junctions, requiring advancing a distal portion of the wire across the junction, then sliding the catheter over the advanced portion of the wire, said guide wire comprising
    a flexible, torqueable proximal wire section between about 50-250 cm in length and formed of a proximal wire core segment having an outer diameter of between about 10-20 mils,
    a more flexible intermediate section having a length between about 20-60 cm and formed, from an intermediate wire-core segment having an average reduced diameter of between about 4-8 mils and about 10-50% of the core's proximal segment, and a flexible polymer covering which encases the intermediate core segment, and provides column strength thereto, and
    a most flexible distal end section having a length between about 1-10 cm and formed from a distal wire core segment having a reduced diameter of between about 26 mils, and a flexible radio-opaque helical coil covering the distal end segment and providing column strength thereto,
    said intermediate section having a hydrophilic polymer surface which makes the section more lubricious than the adjacent distal end segment, and said wire core.

11. A catheter device for use in accessing a target site along a tortuous vessel path which is at least about 20 cm long and which has sharp-bend vessel junctions, said device comprising
    a guide wire having (i) a flexible, torqueable proximal wire section between about 50-250 cm in length and formed of a proximal wire core segment having an outer diameter of between about 10-40 mils, (ii) a more flexible intermediate section having a length between about 20-60 cm and formed from an intermediate wire-core segment having a reduced diameter of between about 4-20 mils and between about 10%-50% of the core's proximal segment, and a flexible polymer covering which encases the intermediate core segment, providing column strength thereto, and (iii) a most flexible distal end section having a length between about 1-10 cm and formed from a distal wire core segment having a reduced diameter of between about 2-6 mils, and a flexible sleeve covering the distal end segment and providing column strength thereto, where the intermediate section has a low-friction polymer surface which makes the section more lubricious than the adjacent distal end segment, and
    a catheter designed to be advanced over the wire, as the wire is moved toward the target site.

12. The device of claim 11, wherein the catheter includes a relatively stiff proximal tube segment dimensioned to track the wire along the proximal end section thereof, and a relatively flexible distal tube segment constructed and dimensioned to track the wire along the intermediate and distal end sections thereof.

13. The device of claim 12, wherein catheter has a substantially constant-diameter inner lumen, and the wire has a substantially constant diameter along its length.

14. The device of claim 13, wherein the clearance between the outer surface of the wire and the inner lumen of the catheter is between about 2-5 mils.

15. The device of claim 12, wherein the clearance between the outer surface of the wire and the inner lumen of the catheter is between about 2-5 mils.

* * * * *